United States Patent [19]
Bardy et al.

[11] Patent Number: 5,356,425
[45] Date of Patent: * Oct. 18, 1994

[54] METHOD AND APPARATUS FOR TREATMENT OF ATRIAL FIBRILLATION AND FLUTTER

[75] Inventors: Gust H. Bardy, Seattle, Wash.; Rahul Mehra, Stillwater, Minn.

[73] Assignee: Medtronic, Inc., Minneapolis, Minn.

[*] Notice: The portion of the term of this patent subsequent to Aug. 2, 2011 has been disclaimed.

[21] Appl. No.: 82,327

[22] Filed: Jun. 24, 1993

Related U.S. Application Data

[63] Continuation of Ser. No. 906,914, Jun. 30, 1992, abandoned.

[51] Int. Cl.$^5$ ............................................. A61N 1/372
[52] U.S. Cl. ............................................................. 607/14
[58] Field of Search .......................... 607/4, 5, 6, 9, 14

[56] References Cited

U.S. PATENT DOCUMENTS

| | | | |
|---|---|---|---|
| 3,878,564 | 4/1975 | Yao et al. | 128/419 B |
| 4,467,807 | 8/1984 | Bornzin . | |
| 4,686,988 | 8/1987 | Sholder | 128/419 PT |
| 4,750,495 | 6/1988 | Moore et al. | 128/419 PG |
| 4,998,974 | 3/1991 | Aker | 128/419 PG |
| 5,203,326 | 4/1993 | Collins . | |

OTHER PUBLICATIONS

"Vagal Tuning" by Bilgutay et al., Journal of Thoracic and Cardiovascular Surgery, vol. 56, No. 1, Jul. 1968, pp. 71–82.
"Carotid Sinus Nerve Stimulation in the Treatment of Angina Pectoris and Supraventricular Tachycardia", by Braunwald et al., Published in California Medicine, vol. 112, pp. 41–50, Mar. 1970.
"Functional Anatomy of the Cardiac Efferent Innervation", by Randall, et al., in Neurocardiology, edited by Kulbértus et al., Futura Publishing Co., 1988.
"Parasympathetic Postganglionic Pathways to the Sinoatrial Node" Bluemel et al., American Journal of Physiol. 259, (Hearth Circ. Physiol. 28) H1504–H1510, 1990.
"Neural Effects on Sinus Rate and Atrial Ventricular Conduction Produced by 20 Electrical Stimulation From a Transvenous Electrode Catheter in the Canine Right Pulmonary Artery", by Cooper et al. published in Circulation Research, vol 46, No. 1, Jan. 1980, pp. 48–57.
Application Ser. No. 07/736,198 by Bennett et al., filed Jul. 26, 1991.
Application Ser. No. 07/673,883 filed by Obel et al., Mar. 22, 1991.
Article "Special Considerations" in Cardiac pacemekers by Harold Siddons et al., pp. 200–217, Charles C. Thomas Publisher.

Primary Examiner—George Manuel
Attorney, Agent, or Firm—Reed A. Duthler; Harold R. Patton

[57] ABSTRACT

A stimulator for applying stimulus pulses to the AV nodal fat pad in response to sensed atrial rate exceeding a predetermined rate, in order to reduce the ventricular rate. The device also includes a cardiac pacemaker which serves to pace the ventricle in the event that the ventricular rate is lowered below a pacing rate, and provides for feedback control of the stimulus parameters applied to the AV nodal fat pad, as a function of the determined effect of the stimulus pulses on the ventricular rate.

21 Claims, 6 Drawing Sheets

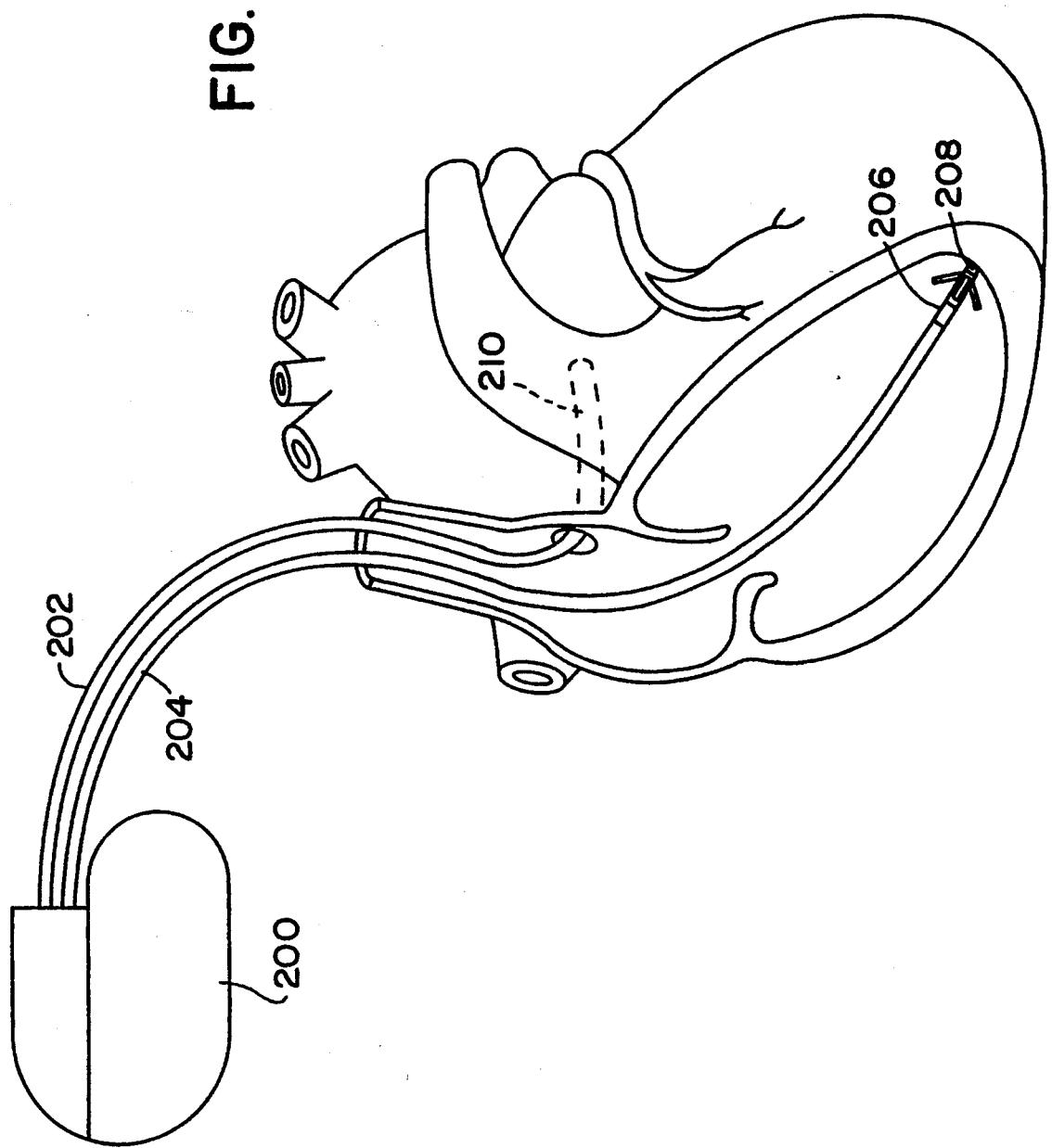

METHOD AND APPARATUS FOR TREATMENT OF ATRIAL FIBRILLATION AND FLUTTER

This is a continuation of copending application Ser. No. 07/906,914 filed on Jun. 30, 1992, now abandoned.

BACKGROUND OF THE INVENTION

This invention relates to implantable stimulators generally and more particularly to implantable nerve stimulators and pacemakers.

It is known that stimulation of the vagus nerve is effective to reduce the sinus rate, as well as to prolong the AV conduction time or, if stimulation energies are high enough, to induce A-V block. Use of vagal nerve stimulation to treat supraventricular arrhythmias and angina pectoris is disclosed in the article "Vagal Tuning" by Bilgutay et al., *Journal of Thoracic and Cardiovascular Surgery*, Vol. 56, No. 1, July, 1968, pp. 71–82. It is also known that stimulation of the carotid sinus nerve produces a similar result, as disclosed in the article "Carotid Sinus Nerve Stimulation in the Treatment of Angina Pectoris and Supraventricular Tachycardia" by Braunwald et al., published in *California Medicine*, Vol. 112, pp. 41–50, March, 1970.

The nervous system regulating the rhythm of the heart also includes a number of highly ganglionated plexi or "fat pads" at various locations on the heart, including fat pads associated with the SA and AV nodes. The fat pad associated with the SA node is located overlying the right pulmonary vein entrance in dogs, and is located along the anterior AV groove in most humans. The fat pad associated with the AV node is located at the junction of the inferior vena cava and the inferior left atrium in dogs, and is located along the posterior AV groove in most humans.

As set forth in "Functional Anatomy of the Cardiac Efferent Innervation" by Randall et al, in *Neurocardiology*, edited by Kulbertus et al, Futura Publishing Co., 1988, direct surgical excision of the fat pad associated with the SA node affects the functioning of the SA node without significantly affecting the AV node. Similarly, excision of the fat pad associated with the AV node affects functioning of the AV node without significantly affecting the SA node.

As set forth in the article "Parasympathetic Postganglionic Pathways to the Sinoatrial Node", Bluemel et al, Am. J. Physiol. 259, (Heart Circ. Physiol. 28) H1504–H1510, 1990, stimulation of the fat pad associated with the SA node results in slowing of the sinus rate without the accompanying prolongation of A-V conduction time which normally results from vagal nerve stimulation. The article also indicates that stimulation of the fat pad associated with the AV node is believed to produce corresponding effects limited to the AV node, i.e. extension of the A-V conduction time without concurrent slowing of the sinus rate.

As set forth in the article "Neural Effects on Sinus Rate and Atrial Ventricular Conduction Produced by Electrical Stimulation From a Transvenous Electrode Catheter in the Canine Right Pulmonary Artery" by Cooper et al., published in Circulation Research, Vol. 46, No. 1, January, 1980, pp. 48–57, the fat pads associated with both the AV node and the SA node may be stimulated by means of electrodes located in the right pulmonary artery. The results obtained include both a depression of the sinus rate and a prolongation of the A-V conduction time in response to continuous stimulation at 2–80 Hz at up 50 ma.

SUMMARY OF THE INVENTION

The present invention responds to detection of a high ventricular rate by stimulating the AV nodal fat pad asynchronously or synchronized to detected ventricular depolarizations. The AV nodal fat pad is located adjacent the posterior AV groove in human hearts. Stimulation may be accomplished by means of a lead carrying electrodes located in the coronary sinus, adjacent the posterior AV groove. Alternatively, fat pad stimulation may be accomplished by means of epicardial or myocardial electrodes applied on or adjacent to the AV nodal fat pad. Other electrode locations may also be workable, as determined empirically.

Stimulation of the AV nodal fat pad results in induction of an increased degree of heart block, decreasing the percentage of atrial depolarizations conducted to the ventricles. The invention thus prevents atrial fibrillation from inducing an inappropriately high ventricular rate. The invention also includes a ventricular pacemaker to assure that the effects of fat pad stimulation do not result in to slow a ventricular rate.

The ventricular rate threshold for initiation of stimulation of the AV nodal fat pad may be fixed or may vary as a function of the sensed atrial rate or the output of a physiologic sensor, such as an activity sensor, respiration sensor, pressure sensor or an oxygen saturation sensor. Alternatively, the fat pad stimulation function may be continuously activated. The sensor may also be used to regulate pacing rate.

The amplitude or frequency of the stimulation pulses directed to the AV nodal fat pad may be selected to produce a sufficient degree of heart block to result in the slowing of the ventricular rate to a rate intermediate the pacing rate defined by the ventricular pacemaker and the ventricular rate required to initiate the fat pad stimulation function. Alternatively, the stimulation level may be selected to slow the intrinsic ventricular rate below the pacing rate such that the pacemaker will control the ventricular rate. Adjustment of the stimulus pulse amplitude or frequency may be accomplished by the physician by means of an external programmer or may be accomplished automatically by the stimulator based on the measured effect of fat pad stimulation on spontaneous ventricular rate.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which:

FIG. 2 is an illustration of one embodiment of a combination ventricular pacing and AV nodal fat pad stimulation lead system for use with the present invention.

DETAILED DESCRIPTION OF THE PREFERRED EMBODIMENTS

Figure 1A:
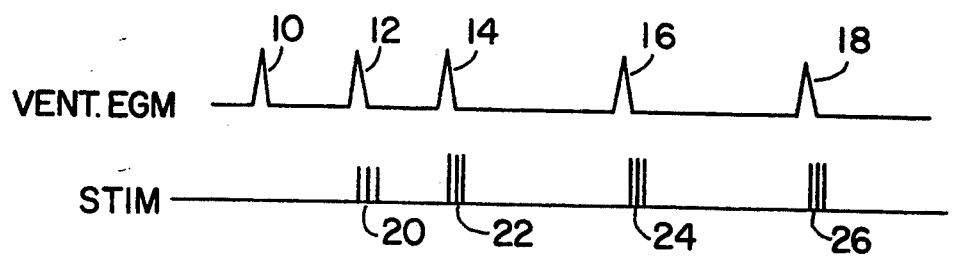
FIGS. 1A–1E include simulated ventricular EGM tracings and timing diagrams, illustrating the basic operation of the present invention.

The present invention is intended to be embodied in a combination pacemaker/fat pad stimulator, particularly adapted for implant in patients suffering from chronic atrial fibrillation or atrial flutter, not satisfactorily treatable by means of drugs. The device senses the occurrence of a rapid ventricular rate and applies stimulation pulses intended to stimulate the fat pad associated with AV node, in order to induce absolute or relative heart block. In the presence of atrial fibrillation, the device operates to decrease the rate at which atrial depolarizations are effective in initiating ventricular contractions.

The device is disclosed in three alternate embodiments. In the first embodiment, on sensing a ventricular rate in excess of a first rate, hereafter the "upper rate", the device begins to deliver burst stimulus pulses to the fat pad associated with the AV node, to induce an increased degree of AV node conduction delay. The stimulus pulses begin at a preset amplitude, and are thereafter increased to a level sufficient to reduce the ventricular rate below a second rate, hereafter the "intermediate rate" greater than the pacing rate defined by the pacemaker. In the first embodiment, induction of complete heart block is not desired. In this embodiment, the stimulus pulse amplitude is adapted to reduce the ventricular rate to an acceptable level, but not necessarily to produce complete heart block. The first embodiment of the present invention is intended to be implanted primarily in patients who undergo repeated episodes of atrial fibrillation or flutter, but in whom atrial fibrillation or flutter is not continuous. By selecting an intermediate rate greater than the pacing rate, it is possible for the device to respond to the termination of atrial fibrillation and the corresponding decrease in spontaneous ventricular rhythm and to terminate burst stimulation.

In the second embodiment of the present invention, intended for use in patients in whom atrial fibrillation is more or less continuous, stimulation of the fat pad associated with the AV node is intended to induce heart block to the degree necessary to allow the pacemaker portion of the device to determine the ventricular rate. In this embodiment, it is particularly desirable that the pacemaker include a sensor of a physiologic parameter related to demand for cardiac output, such as an activity sensor, a respiration sensor or an oxygen saturation sensor. Because the patient's ventricular rate is regulated by means of the pacemaker, it is no longer possible to determine cessation of atrial fibrillation by monitoring the spontaneous ventricular rhythm. As an option, the device may be provided with a timer which periodically interrupts burst stimulation for a time period sufficient to monitor the underlying ventricular rhythm to determine whether it is appropriate, and, if the rate is appropriate to cease burst stimulation until the ventricular rate again exceeds the upper rate.

A third possible embodiment of the present invention simply omits the ability of the device to automatically enter and exit the burst stimulation modality. In such a device, burst stimulation would be provided at all times, and the cardiac pacemaker would simply provide a base ventricular rate. Again, in this embodiment, a pacemaker which varied its pacing rate as a function of measured physiologic demand for oxygenated blood would be particularly desirable.

As a practical matter, it is anticipated that commercial versions of the invention will respond primarily to measured R—R intervals, rather that measuring rate per se. Therefore, the device disclosed below measures ventricular rhythm by comparing measured R—R intervals to a first interval corresponding to the upper rate, hereafter the "upper rate interval", to a second interval corresponding to the intermediate rate, hereafter the "intermediate rate interval" and/or to a third interval corresponding to the pacing rate, hereafter the "pacing interval".

It is also anticipated that actual commercial embodiments of the invention would allow selection between the three embodiments discussed above by means of an external programmer, with the physician selecting the mode of operation most appropriate to the patient in whom the device is implanted.

FIG. 1A illustrates the operation of the first embodiment of the invention, in response to sensing of rapid ventricular rhythm in excess of the upper rate as indicated by closely spaced simulated ventricular depolarizations (R-waves) 10, 12 and 14. With R-wave 12, it is assumed that the device has detected a predetermined number of successive R—R intervals less than the upper rate interval and in response has activated the burst stimulation function.

A first burst of stimulus pulses 20 is delivered synchronized to R-wave 12. Burst 20 is preferably delivered while the ventricles are refractory to stimulation, within 10 to 50 milliseconds following the sensing of the R-wave. As illustrated, the amplitude of pulse burst 20 was not sufficient to significantly affect the ventricular rhythm, as indicated by the timing of R-wave 14. Therefore, the amplitude of the pulses within the next burst 22 is increased. As indicated by the prolonged interval between R-waves 14 and 16, it appears that an increased degree of heart block has been produced, i.e., heart block may have been increased from 2 to 1 to 4 to 1. Because the intervals separating R-waves 14 and 16 and R-waves 16 and 18 exceed the upper rate interval and are less than the intermediate interval, stimulus pulse bursts 24 and 26, synchronized to R-waves 16 and 18, are delivered at the same amplitude as stimulus pulse burst 22.

Figure 1B:
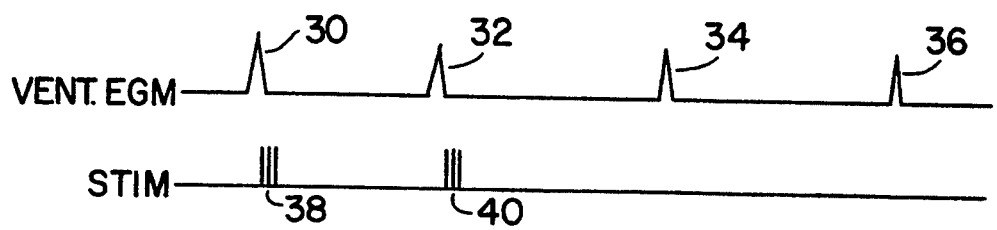

FIG. 1B shows the operation of the first embodiment of the invention in response to a reduction in the spontaneous ventricular rate. R-waves 30 and 32 are separated by an interval less than the intermediate interval and therefore are accompanied by stimulus bursts 38 and 40. R-waves 32 and 34 and R-waves 34 and 36 are separated by intervals which are greater than the intermediate interval and thus do not evoke corresponding stimulus bursts. Moreover, the occurrence of a predetermined number of such extended R—R intervals without accompanying burst stimulation is interpreted by the device as indicating the return of the ventricular rhythm to an appropriate rate and results in the turn off of the burst stimulus function. The return to a lower ventricular rate may be as a result of either an increased degree of naturally occurring heart block between the atrium and the ventricle, a change in the nature of the atrial fibrillation, or cessation of atrial fibrillation. Regardless of the cause, the ability of the device to cease burst stimulation when not required is believed to provide a valuable mechanism for reducing battery drain to prolong device life.

Figure 1C:
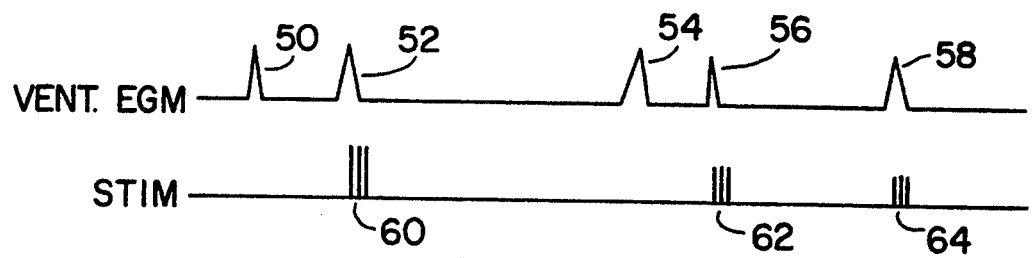

FIG. 1C illustrates the operation of the first embodiment of the invention, in the situation in which stimulus pulses induce heart block to the degree that the R—R interval following stimulation exceeds the intermediate rate interval. R-waves 50 and 52 are separated by interval in excess of the upper rate required to activate the burst pacing function. A first burst 60 is delivered synchronized to R-wave 52, resulting in induction of complete heart block for the following heart cycle. Therefore, the pacemaker provides a pacing pulse at 54 followed by an evoked depolarization. Because the interval separating R-wave 52 and paced R-wave 54 is greater than the intermediate interval, no stimulus burst is delivered synchronous to the paced R-wave at 54. In response to the occurrence of the next subsequent R-wave 56, defining the endpoint of an R—R interval less than the intermediate interval, a pulse burst 62 is delivered, but at a lower amplitude. Because R-waves 56 and 58 are separated by an interval less than the intermediate interval, a pulse burst is delivered at 64, synchronized to R-wave 58. The amplitude of the pulse burst is not changed from burst 62.

As such, the operation of the first embodiment of the invention, as illustrated in FIGS. 1A through 1C, provides for automatic regulation of the burst stimulation pulses to accomplish a reduction in ventricular rate to a point at which the ventricular rate lies below the upper rate required for activation of the burst pacing function, but above the intermediate rate. This allows for detection of the return of a more normal ventricular rhythm to inhibit the burst stimulus function.

Figure 1D:
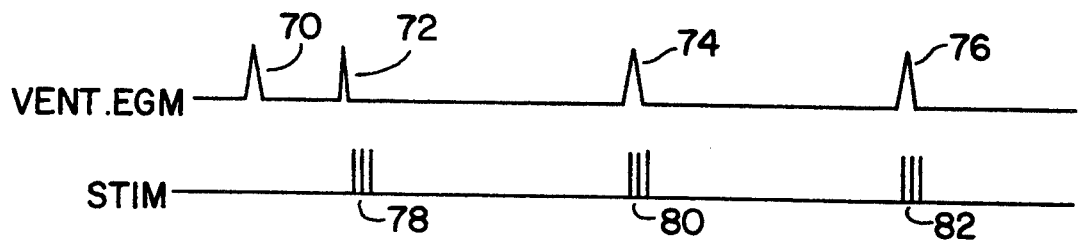
Figure 1E:
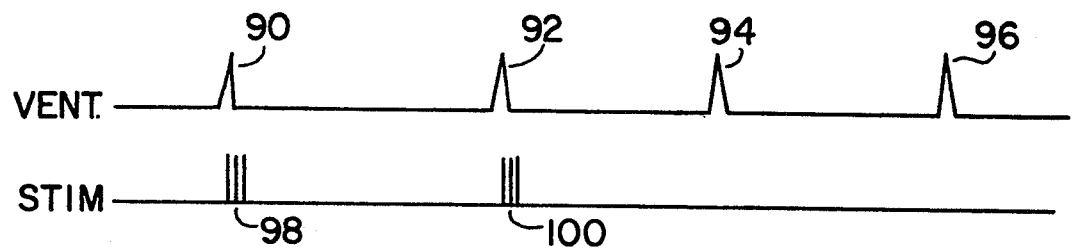

FIGS. 1D and 1E illustrate the second embodiment of the present invention, in which stimulus pulse amplitude is adjusted to produce a degree of heart block sufficient to reduce the spontaneous ventricular pacing rate below the pacing rate. FIG. 1D illustrates the occurrence of a high ventricular rate as indicated by closely spaced R-waves 70 and 72, and the corresponding activation of the burst stimulus function, indicated by delivery of a stimulus pulse burst 78. Pulse burst 78 should be understood to be of sufficient amplitude to reduce the ventricular spontaneous rhythm for the following cardiac cycle to a rate below the pacing rate. As a result, the escape interval of the associated pacemaker times out resulting in a paced R-wave at 74.

In this embodiment of the invention, stimulation bursts are delivered synchronized to paced R-waves, as illustrated by pulse bursts 80 and 82, synchronized to R-waves 74 and 76. Assuming that the pacemaker associated with the fat pad stimulator is a rate responsive pacemaker, capable of varying the pacing rate in response to patient's demand for oxygenated blood, a reasonably normal heart rate should be provided.

FIG. 1E illustrates the operation of the second embodiment of the device, in circumstances in which the inappropriately high ventricular rhythm has disappeared. In FIG. 1E, it should be assumed that burst stimulus pulses 98 and 100 are delivered associated with paced R-waves 90 and 92 based on earlier activation of the burst stimulus function as illustrated in FIG. 1D. In this embodiment of the invention, a timer is optionally provided, initiated on activation of the burst stimulus function. On expiration of a predetermined interval following activation of the burst stimulus function, the timer turns the burst stimulus function off in order to allow the underlying ventricular rhythm to resurface. If, as indicated in FIG. 1E, the natural ventricular rate is not excessively rapid (not in excess of the upper rate, in this case), the burst pacing function may remain disabled until a ventricular rate in excess of the upper rate reappears.

The third embodiment of the present invention as discussed above simply omits all automatic activation and deactivation functions associated with the burst stimulus function, and assumes that synchronized burst stimulus pulses will be applied continuously. Adjustment of the amplitude of the burst pulses may be accomplished by the physician at the time of implant or may be automatically performed by the implanted device, using the adjustment criteria discussed in conjunction with FIGS. 1D and 1E. The operation of such a device can also be understood by a review of FIG. 1D, assuming that activation of the burst stimulus function occurs as a result of an external programming command after R-wave 70. The device will simply continue to pace at the sensor determined pacing rate and to deliver synchronized burst stimulus pulses until reprogrammed.

FIG. 2 is a cutaway view of the heart illustrating an implantable pacemaker/fat pad stimulator and an associated lead system. The fat pad stimulator 200 is provided with two endocardial leads 202 and 204. Lead 202 is a coronary sinus lead carrying a single electrode or a pair of electrodes adapted to be located in the coronary sinus in the region indicated at 210. Lead 204 is a standard ventricular pacing lead, provided with a bipolar electrode pair comprising electrodes 206 and 208. Electrodes 206 and 208 are used for sensing of ventricular depolarizations and for pacing the ventricle. The electrode or electrodes located on lead 202 are employed to stimulate the fat pad associated with the AV node in order to increase the degree of heart block, as discussed above. If only one electrode is provided on lead 204, it may be paired with an electrode on the housing of stimulator 200. If two electrodes are provided, they will serve as a bipolar pair for stimulating the AV nodal fat pad.

Figure 3:
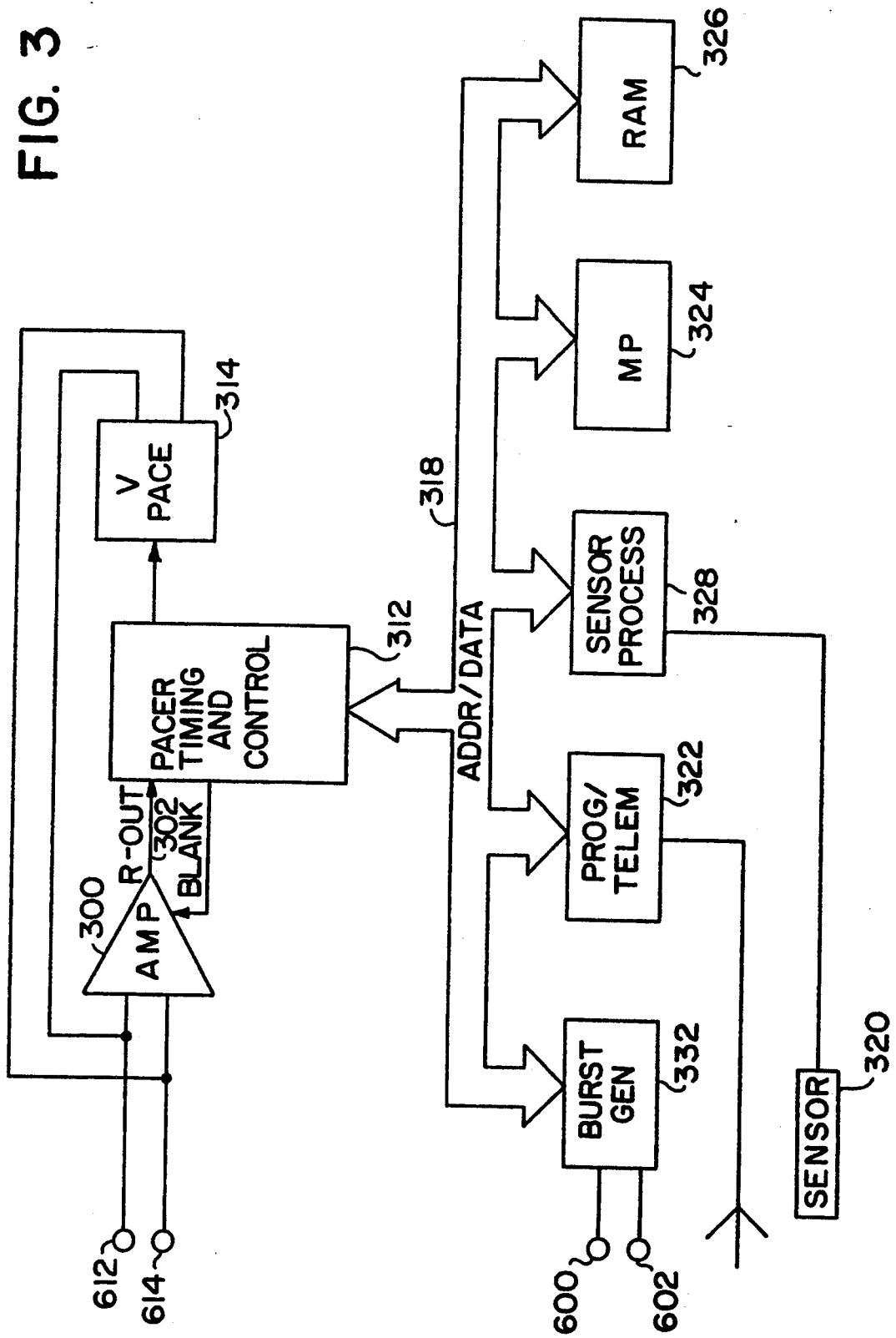
FIG. 3 is a functional block diagram illustrating an implantable pacemaker/fat pad stimulator in which the present invention may be embodied.

FIG. 3 is a functional schematic diagram of an implantable pacemaker/fat pad stimulator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemakers and/or pacemaker/cardioverter/defibrillators presently commercially sold or being implanted for clinical evaluation in the United States.

The device is provided with a pair of electrode for fat pad stimulation including electrodes 600 and 602, as discussed in conjunction with FIG. 2. Alternatively electrodes 600 and 602 may be epicardial or myocardial electrodes applied to or adjacent to the fat pad associated with the AV node.

Electrodes 612 and 614 are located on or in the ventricle and are coupled to the R-wave amplifier 300, which preferably takes the form of a gain controlled amplifier providing an adjustable sensing threshold as a function of the measured R-wave amplitude. A signal is generated on R-out line 302 whenever the signal sensed between electrodes 612 and 614 exceeds the present sensing threshold.

The bandpass characteristics of amplifier 300 are optimized for sensing R-waves. The general operation of the R-wave amplifier 300 may correspond to any of the numerous sense amplifiers employed in prior art pacemakers.

Burst generator 332 may employ any appropriate technology for generation of stimulation pulses in the form of individual pulses or pulse trains, having amplitudes up to 30 ma, pulse widths of up to 2 ms, and frequencies of up to 1000 Hz. For example, the Medtronic Model 5325 Programmable Stimulator, as discussed in the above cited Cooper et al. reference includes circuitry for generating appropriate stimulation pulses and trains. Given that circuitry for pulse generation has become well known to those skilled in the art, no detailed disclosure is included herein. The specific timing, amplitude, duration and number of pulses is controlled by microprocessor 324 via data bus 318, under the control of a program stored in memory 326. The programming stored in memory 326 may be altered by means of programming/telemetry circuitry 322, which may correspond to similar circuitry in presently marketed implantable pacemakers.

Much of the remainder of the circuitry is dedicated to the provision of cardiac pacing therapies, which for purposes of the present invention may correspond to the prior art. The pacer timing/control circuitry 312 includes programmable digital counters which control the basic time intervals associated with VVI pacing. Circuitry 312 also may optionally also control escape intervals associated with antitachyarrhythmia pacing in the ventricle, employing any antitachyarrhythmia detection and pacing therapies known to the art.

Intervals defined by pacing circuitry 312 include ventricular pacing escape intervals, the refractory periods during which sensed R-waves are ineffective to restart timing of the escape intervals and intervals corresponding to the widths of the pacing pulses. The durations of these intervals are determined by microprocessor 326, in response to stored data in memory 326 and optionally in response to a physiologic sensor 320, such as an oxygen saturation sensor, a respiration sensor, or a physical activity sensor, of types well known to the art. The sensor signals are processed by sensor processing circuitry 328 to produce a signal indicative of the patient's physiologic demand for oxygenated blood, and this signal in turn may be used to correspondingly regulate the pacing rate, as set forth in U.S. Pat. No. 4,467,807 issued to Bornzin, incorporated herein by reference in its entirety. The durations of the intervals to be timed are communicated to the pacing circuitry 312 via address/data bus 318. Pacer circuitry 312 also determines the amplitude of the cardiac pacing pulses under control of microprocessor 324.

During pacing, the escape interval counter within pacer timing/control circuitry 312 is reset upon sensing of R-waves as indicated by signals on line 302 and on timeout triggers generation of pacing pulses by pacer output circuitry 314, coupled to electrodes 612 and 614. The escape interval counter is also reset on generation of pacing pulses, and thereby controls the basic timing of cardiac pacing functions, including any antitachycardia pacing functions. The values of the counts present in the escape interval counter when reset by sensed R-waves or delivered pacing pulses may be used to measure the durations of R—R intervals.

Microprocessor 324 operates as an interrupt driven device, and is awakened by interrupts from pacer timing/control circuitry 312 corresponding to the occurrence of sensed R-waves and corresponding to the generation of cardiac pacing pulses. These interrupts are provided via data/address bus 318. Any necessary mathematical calculations to be performed by microprocessor 324 and any updating of the values or intervals controlled by pacer timing/control circuitry 312 take place following such interrupts.

For example, in response to a sensed or paced ventricular depolarization or R-wave, the intervals separating that R-wave from the immediately preceding R-wave, paced or sensed (R—R interval) may be stored. In the event that the preceding series of R-waves are indicative of a ventricular rhythm in excess of a predetermined upper rate, the microprocessor 324 may activate the fat pad stimulation function, and, while the stimulation function is activated will control burst generator 332 to provide pulse bursts synchronized to subsequent detected R-waves, when appropriate.

The measured values of the stored R—R intervals may also be used to determine the efficacy of the fat pad stimulation in reducing ventricular rate, and thereby may be used to regulate the amplitude of the burst pacing pulses, as discussed above in conjunction with FIGS. 1A through 1E. Similarly, the duration of the R—R intervals may be used to indicate a return of a spontaneous ventricular rate which is outside the range requiring stimulation of the AV nodal fat pad, allowing microprocessor 324 to turn off the fat pad stimulation function.

Figure 4A:
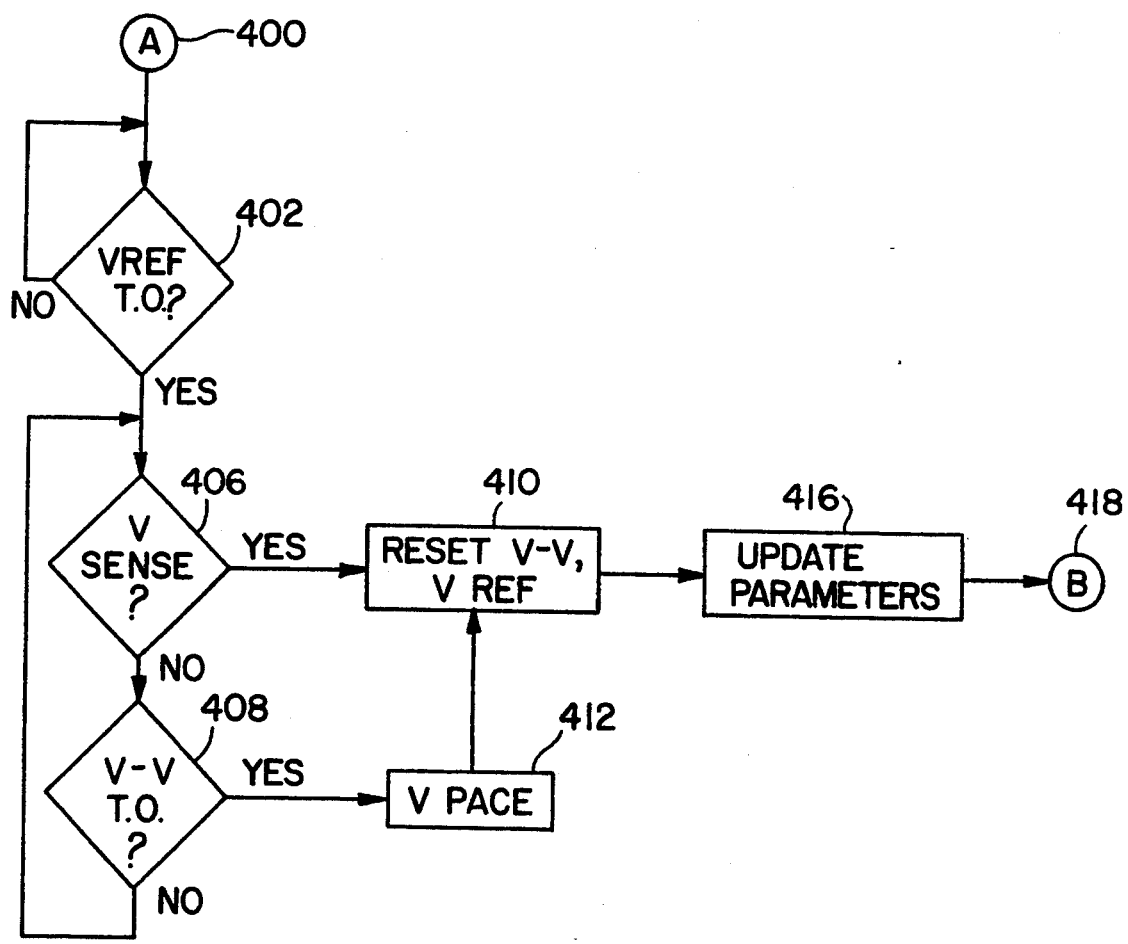
FIGS. 4A–4C are functional flow charts illustrating various methods of operation of the device illustrated in FIG. 3.
Figure 4B:
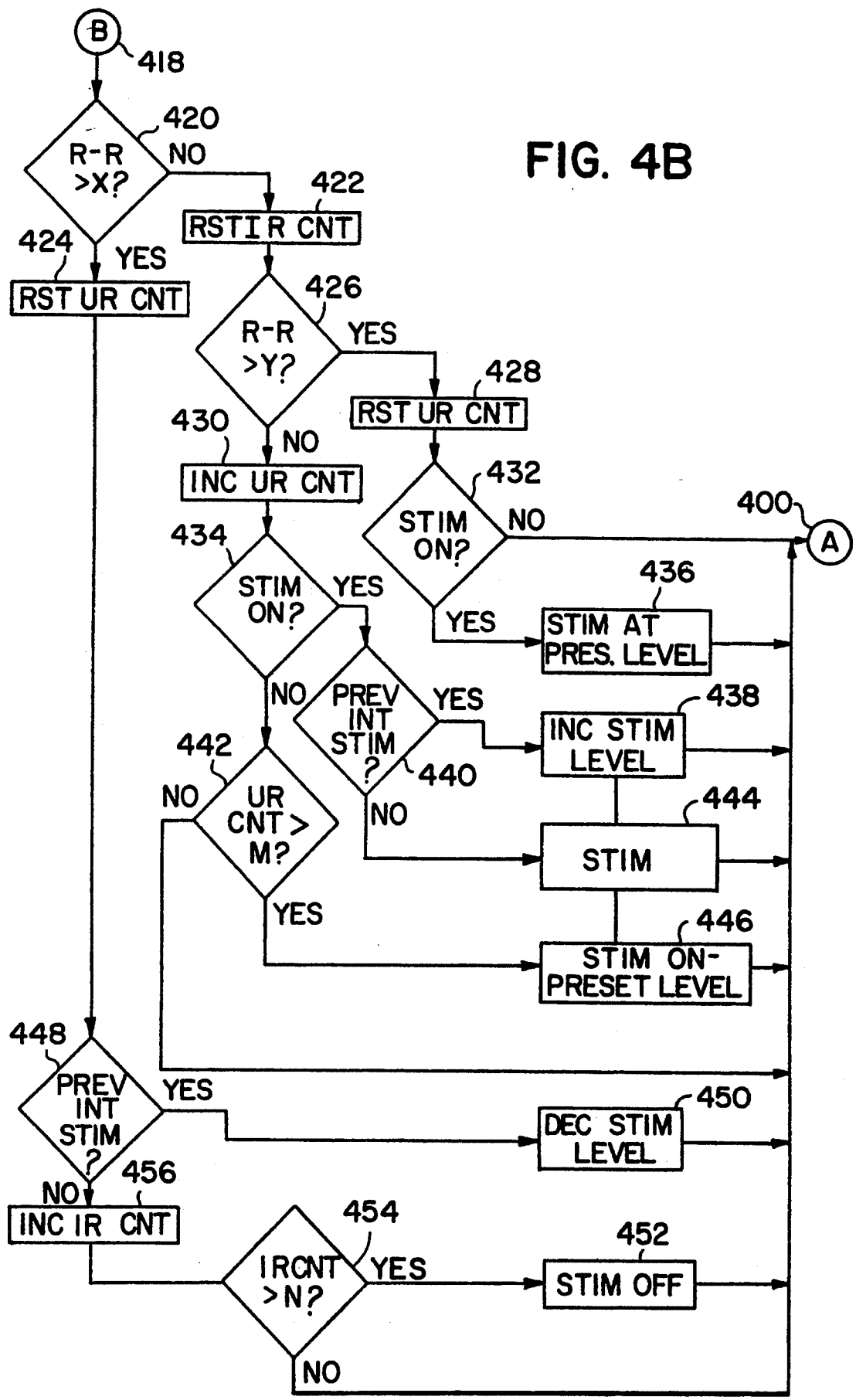
Figure 4C:
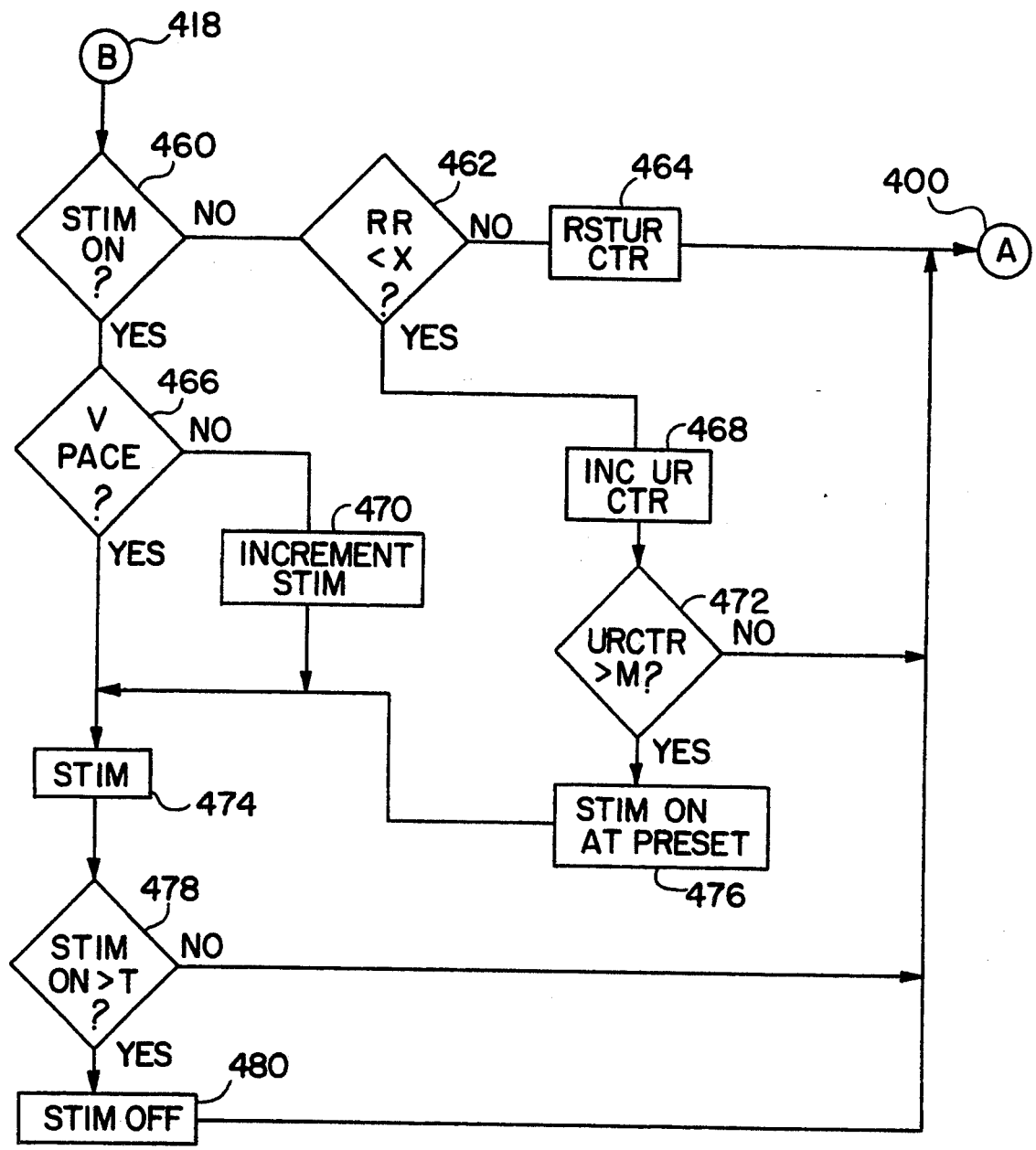

FIGS. 4A, 4B and 4C are a functional flow chart illustrating the basic operation of the first, second and third embodiments of the invention, discussed above. FIG. 4A is common to all embodiments. FIG. 4B illustrates the operation of the burst stimulation function in the first embodiment. FIG. 4C illustrates a modification to FIG. 4B, setting forth the operations of the second embodiment, discussed above and with certain functions disabled, illustrating the operation of the third embodiment as well.

FIG. 4A is a functional diagram illustrating the basic operation of the cardiac pacing function of the present invention. The flow chart as illustrated is entered at 400, shortly following the delivery of a cardiac pacing pulse or the sensing of a spontaneous ventricular depolarization (R-wave). At this point, the ventricular refractory period, extending following either a ventricular pacing pulse or a sensed ventricular depolarization is in effect. Similarly, the escape interval, initiated on the sensing of ventricular depolarization or the delivery of a ventricular pacing pulse has also been reinitiated. During the refractory period, sensed ventricular depolarizations will be ineffective to restart the escape interval timer. Following expiration of the refractory period at 402, a sensed R-wave will be effective to reset the escape interval timer. Following the refractory period, the microprocessor awaits an interrupt indicative of either a sensed R-wave at 406 or expiration of the escape interval at 408. If an R-wave is sensed at 406 prior to expiration of the escape interval, the escape interval and ventricular refractory interval are reset at 410, and the value of the escape interval and refractory interval are updated at 416 if appropriate. For example, in those embodiments in which a physiologic sensor is provided, a new escape interval may be specified at this time in response to a change in the patient's indicated physiologic demand for cardiac output.

Similarly, the values in effect for the upper rate interval and intermediate interval may also be varied in conjunction with the pacing rate, so that the criteria for activation and disabling of the burst stimulation function are based on the degree of divergence of the ventricular rhythm from a sensor determined rate. In such cases, the values of the upper rate interval and intermediate interval will likewise be updated at 416, prior to entry to the burst pacing subroutine.

In the event that the escape interval times out at 408 prior to the sensing of an R-wave, a ventricular pacing pulse is triggered at 412, and the escape interval and refractory period are reset at 410, as discussed above. Again, following reset of the escape interval and refractory period, parameters may be updated, if appropriate, at 416. Following update of the escape interval and refractory period at 416, the device enters the burst pacing subroutine at 418.

The flow chart of FIG. 4B is entered at 418, following delivery of a pacing pulse or sensing of an R-wave. The value of the previous R—R interval is evaluated at 420 to determine whether it is greater than the intermediate interval as discussed above. The duration of the intermediate interval may be fixed or may vary with the escape interval, in the event that the pacemaker is provided with a physiologic sensor. For example, this rate might be fixed at 130 beats per minute, or might be equal to the sensor indicated pacing rate plus 20 beats per minute. These values are chosen merely as examples of possible parameter settings. It is to be understood that the physician will select the particular rates and corresponding intervals based upon an evaluation of the needs and condition of the individual patients in whom the device is implanted.

In the event that the most recent R—R interval is greater than the intermediate interval, the upper rate count is reset at 424. This count reflects the number of sequential R—R intervals corresponding to ventricular events occurring at a rate above the upper rate, as discussed above.

At 448, the microprocessor checks to determine whether the ventricular event (paced or spontaneous R-wave) initiating the preceding R—R interval was accompanied by delivery of burst stimulation pulses. If so, the occurrence of an R—R exceeding the intermediate interval is taken as indicative of the fact that the burst stimulation pulse is excessive in amplitude. Therefore, at 450, the stimulation pulse level is decremented so that the next delivered stimulus burst occurs at a lower amplitude. This much of the device corresponds generally to the simulated EGM and timing diagram illustrated in FIG. 1B.

In the event that the ventricular event initiating the previous R—R interval was not accompanied by burst stimulation at 448, the intermediate rate counter is incremented at 456 indicating the occurrence of an R—R interval greater than the intermediate interval and not accompanied by burst stimulation. The microprocessor checks at 454 to determine whether the intermediate rate count is greater than "N" typically equal to a count of 1–3. A count of "N" or greater is taken as an indication that the spontaneous ventricular rhythm has fallen below the intermediate rate and therefore, the burst stimulation function is turned off at 452. Subsequent activation of the burst stimulation mode will require detection of a spontaneous ventricular rate in excess of the upper rate discussed above. In the event that the intermediate rate count is less than "N" the device simply returns to bradycardia pacing at 400, and performs the functions described in conjunction with FIG. 4A.

In the event that the detected R—R interval is less than the intermediate interval at 420, the intermediate rate counter is reset at 422, and the stored R—R interval is compared to the upper rate interval at 426. If the R—R interval greater than the upper rate interval, the upper rate counter is reset at 428 and the microprocessor determines whether the burst stimulation function is presently activated at 432. If so, burst stimulation is delivered at 436 synchronized to the previously occurring ventricular depolarization. This aspect of the operation of the device corresponds to the latter portion of FIG. 1A. Because the R—R interval lies between the upper rate interval and the intermediate interval, the device determines that the stimulation level is appropriate, and therefore does not adjust the stimulation level.

In the event that the detected R—R interval is less than the upper rate interval, the upper rate counter is incremented at 430, and the microprocessor checks at 434 to determine whether the stimulator was previously activated. If so, this is taken as an indication that the stimulus amplitude is inadequate, as it has not reduced the ventricular rate below the upper rate. Therefore, the stimulus pulse amplitude is incremented at 438, and an incremented stimulus pulse amplitude is delivered at 444, with the device returning to bradycardia pacing thereafter at 400. This portion of the flowchart corresponds to the operation of the device illustrated in the first portion of FIG. 1A, which shows the implementation and pulse amplitude in response to the failure of the initial pulse to produce a prolongation of the R—R interval.

In the event that stimulation has not been previously activated at 434, the microprocessor checks at 442 to determine whether the upper rate count exceeds a predetermined minimum value "M" typically equal to 5–20, necessary to activate the burst stimulation function. If so, the burst stimulation function is activated at 446, and a stimulation pulse is delivered at 444 at a preset level. This portion of the operation of the device corresponds to the initiation of stimulation, as illustrated in FIGS. 1A, 1C and 1D. It is anticipated that the preset stimulation level would be determined by the physician, and be subject to incrementation or decrementation depending upon the response of the ventricular rate. In the event that the upper rate count has not reached "M" at 442, the device simply returns to bradycardia pacing at 400.

As such, FIG. 4B describes a device in which a predetermined number "M" of sequential R—R intervals having a value less than or equal to the upper rate interval is required in order to activate the burst stimulator. Similarly, a predetermined number, "N" of sequential intervals greater than the intermediate interval will result in disabling or turning off the burst stimulation function. The upper rate and intermediate intervals are also used to monitor the response of the ventricular rhythm to burst stimulation, and are used to increment or decrement the burst pulse amplitude.

FIG. 4C illustrates a modification to the flow chart of FIG. 4B, in order to illustrate the operation of the second embodiment of the invention. In FIG. 4C, only the portion of the flow chart which differs from that illustrated in FIG. 4B is shown. Functional blocks labelled identically to those illustrated in FIG. 4B correspond to those illustrated in 4B. The flow chart is entered at 418 corresponding to the entry point for the flow chart illustrated in FIG. 4B. However, the operation thereafter differs significantly.

At 460, the microprocessor checks to determine whether the burst stimulation function has been activated. If so, the device checks at 466 to determine whether the previous R—R interval ended with a ventricular pacing pulse. If not, the device determines that the stimulation pulse amplitude has been ineffective to reduce the ventricular rhythm sufficiently and therefore increments the stimulation amplitude at 470. A stimulation pulse burst is delivered at 474 with incremented amplitude.

If the previous R—R interval ended with a ventricular pacing pulse, the device determines that the stimulation pulse amplitude has been sufficient to allow the pacemaker, preferably a rate responsive pacemaker, to determine the ventricular rate. Therefore, stimulation is delivered at 474 at the previously adjusted amplitude. This portion of the operation of the flow chart corresponds to the operation of the device as illustrated in the later portion of the tracings illustrated in FIG. 1B.

After delivery of the stimulus burst, the microprocessor checks at 478 to determine whether the stimulation function has been on for greater than a predetermined time "T". If so, burst stimulation is disabled at 480 in order to determine whether the intrinsic ventricular rate has slowed to the point where burst stimulation is no longer required. As illustrated, this would correspond to any rate below the upper rate. This corresponds to the operation of the device as illustrated in FIG. 1E.

If the stimulation function is not activated, the previously measured R—R interval is checked at 462 to determine whether it is less than upper rate interval. If so, the upper rate counter is incremented at 468 and compared to a predetermined value "M" at 472 to determine whether burst stimulation should be activated. If the upper rate count exceeds "M", the burst stimulation function is turned on 476, and burst stimulation is delivered at 474. If not, the device simply returns to bradycardia pacing at 400. This portion of the operation of the device corresponds to the initiation of burst stimulation as illustrated in FIG. 1D.

As such, FIG. 4C describes a device in which burst stimulation is activated in response to the occurrence of a predetermined number "M" of R—R intervals less than the upper rate interval. Following activation of burst stimulation, the stimulus amplitude is incremented until a sufficient degree of heart block is induced to allow the associated ventricular pacemaker to assume control of the ventricular rhythm. Periodically, the burst pacing function is disabled in order to determine whether the underlying ventricular rhythm has returned to a level below the upper rate necessary for activation of burst stimulation.

As discussed above, a third embodiment of the invention may simply produce burst stimulation synchronized to all detected ventricular events, with the amplitude set by the physician at a level determined to be sufficient to induce heart block or automatically adjusted by the device to produce the same result. While no separate flow chart is illustrated, the flow chart of FIG. 4C could be adapted to produce such function by simply specifying that the stimulation function is locked on at all time, so that the function of disabling the stimulation at 480 is deleted and such that the stimulation function check at 460 always yields a positive result.

In all three embodiments discussed above, it is likely, even if not required, that the burst stimulation function will be activated for extended periods of time. In other areas of nerve stimulation, a phenomenon known as accommodation has been found to occur, wherein the efficacy of the stimulation falls off with time. Thus, it may be desirable in the context of the present invention to provide for measures to prevent accommodation.

It is believed that accommodation may be countered in a number of ways. For example, the amplitude and pulse width of the stimulus pulses may be varied cyclically, with increasing as amplitude is decreased and vice versa, as is currently done in commercially available nerve stimulators. Alternatively, the burst function may be periodically disabled at regular interval. Another alternative approach would be to monitor the output amplitude of the burst pulses and, if maximum amplitude pulses are delivered for an extended period of time without accomplishing the desired slowing of the ventricular rate, the burst stimulation function may be temporarily disabled. All of these approaches are readily implemented in a microprocessor controlled device as illustrated in FIG. 3, or could be implemented in hardware form within the burst generator itself, in a manner analogous to available nerve stimulators, if accommodation should prove to be a problem clinically.

While the above device is disclosed in the context of a single chamber ventricular pacemaker, it is believed that the invention may also be usefully be practiced in the context of a dual chamber pacemaker or in the context of an implantable pacemaker/cardioverter/defibrillator. Further, while the embodiment of the invention described relies on sensing of high ventricular rate to activate the burst pacing function, it is believed that the burst pacing function may also be usefully activated in response to detection of atrial fibrillation using one or more atrial electrodes.

In addition, while the device is described in the form of a microprocessor based programmable stimulator, the operation of the invention is sufficiently simple that it could readily be embodied in the form of a full custom digital integrated circuit based device or even a device employing analog timing circuits. Therefore, the above disclosure should be considered exemplary, rather than limiting with regard to the claims below.

In conjunction with the above disclosure, I claim:

1. A method of electrical stimulation, comprising:
   placing an electrode in an appropriate location for stimulating the AV nodal fat pad of a human heart;
   defining a first heart rate;
   sensing the rate at which said human heart is beating; and
   providing said stimulus pulses to said electrode, synchronized to depolarizations of a chamber of said human heart in response to the rate at which said heart is beating exceeding said first heart rate.

2. A method according to claim 1 wherein said pulse providing step comprises delivering said stimulus pulses during refractory periods following depolarizations of said chamber of said human heart.

3. A method according to claim 1 or claim 2 further comprising the steps of:
   defining a second heart rate below said first heart rate; and
   pacing said human heart when the rate at which said human heart is beating falls below said second heart rate.

4. A method according to claim 3 further comprising the step of defining a third heart rate above said second heart rate, and wherein said step of providing said stimulus pulses to said electrode is continued only while the rate of said human heart is above said third rate.

5. A method according to claim 1, further comprising the steps of;

determining the effect of said stimulus pulses on the rate at which said human heart is beating; and adjusting the amplitude of said stimulus pulses as a function of the determined effect of said stimulus pulses.

6. A method according to claim 5 wherein said step of determining the effect of said stimulus pulses on the rate of said human heart comprises comparing the rate of said human heart following delivery of said stimulus pulses to a predetermined upper rate and wherein said adjusting step comprises incrementing the amplitude of said stimulus pulses responsive to the failure of said stimulus pulses to reduce the rate of said human heart below said upper rate.

7. A method according to claim 6 wherein said step of determining the effect of said stimulus pulses on the rate of said human heart comprises comparing the rate of said human heart following delivery of said stimulus pulses to an intermediate heart rate less than said upper rate and wherein said adjusting step comprises decrementing the amplitude of said stimulus pulses in response to delivery of said stimulus pulses resulting in a reduction in a rate of said human heart below said intermediate rate.

8. An electrical medical stimulator, comprising:
electrode means for delivery of electrical stimulation to the fat pad associated with the AV node of a human heart;
pulse generator means for generating stimulus pulses and for providing said stimulus pulses to said electrode means;
means for sensing the rate at which said human heart is beating;
means for defining a first heart rate; and
initiating means responsive to said sensing means for initiating the operation of said pulse generator means in response to the rate of said human heart exceeding said first heart rate;
means for defining a second heart rate;
means for pacing the ventricle of said human heart when the rate of said human heart falls below said second heart rate; and
means for defining a third heart rate above said second rate and below said first rate, such that said pulse generator means provides said stimulus pulses to said electrode means only when the rate of said human heart is above said third rate.

9. An electrical medical stimulator, comprising:
electrode means for delivery of electrical stimulation to the fat pad associated with the AV node of a human heart;
means for sensing depolarizations of a chamber of said human heart to determine the rate at which said human heart is beating;
pulse generator means responsive to said sensing means for generating stimulus pulses and for providing said stimulus pulses to said electrode means during the refractory period of said chamber of said heart;
means for defining a first heart rate; and
initiating means responsive to said sensing means for initiating the operation of said pulse generator means in response to the rate of said human heart exceeding said first heart rate.

10. An electrical medical stimulator, comprising:
electrode means for delivery of electrical stimulation to the fat pad associated with the AV node of a human heart;
means for sensing depolarizations of a chamber of said human heart to determine the rate at which said human heart is beating;
pulse generator means for generating stimulus pulses and for providing said stimulus pulses to said electrode means;
means for defining a first heart rate;
initiating means responsive to said sensing means for initiating the operation of said pulse generator means in response to the rate of said human heart exceeding said first heart rate; and
means for sensing a physiologic parameter other than heart rate; and
wherein said means for defining said first heart rate comprises means for defining said first heart rate as a function of said physiologic parameter.

11. A stimulator according to claim 8 or claim 9 or claim 10, further comprising means responsive to said sensing means and to said pulse generator means for determining the effect of said stimulus pulses on the rate of said human heart and means for adjusting the energy of said stimulus pulses as a function of the detected effect of said stimulus pulses.

12. A stimulator according to claim 11 wherein said determining means comprises means for comparing the rate of said human heart following delivery of said stimulus pulses to a predetermined upper rate, and wherein said adjusting means is responsive to the failure of delivered stimulus pulses to reduce the heart rate of said human heart below said upper rate and in response thereto increments the energy of said stimulus pulses.

13. A stimulator according to claim 12 further comprising means for defining an intermediate rate below said upper rate and wherein said determining means compares the rate of said human heart following delivery of said stimulus pulses to said intermediate heart rate and, in response to delivery of said stimulus pulses resulting in a reduction of the rate of said human heart below said intermediate rate decrements the energy of said stimulus pulses.

14. A stimulator according to claim 13 further comprising means for defining a pacing rate below said intermediate rate and means for pacing said human heart when the rate of said human heart falls below said pacing rate.

15. An electrical medical stimulator, comprising:
electrode means for delivery of electrical stimulation to the fat pad associated with the AV node of a human heart;
means for sensing depolarization of a chamber of said human heart to determine the rate at which said human heart is beating;
pulse generator means responsive to said sensing means for generating stimulus pulses and for providing said stimulus pulses to said electrode means;
means for defining a first heart rate;
means for defining an acceptable range of heart rates;
initiating means responsive to said sensing means for enabling the operation of said pulse generator means in response to the rate of said human heart exceeding said first heart rate; and
means responsive to said sensing means and to said pulse generator means for determining the effect of said stimulus pulses on the rate of said human heart and means for adjusting the energy of said stimulus pulses, while said pulse generator is enabled, as a function of the determined effect of said stimulus pulses, to maintain said heart rate within said acceptable range of heart rates.

16. A stimulator according to claim 8 or claim 9 or claim 10 or claim 15 wherein said means for sensing the rate of said human heart comprises means for sensing ventricle depolarizations of said human heart.

17. A simulator according to claim 9 or claim 10 or claim 15 further comprising means for defining a second heart rate and means for pacing said human heart when said sensed heart rate falls below a second heart rate.

18. A stimulator according to claim 17 wherein said pacing means comprises means for pacing the ventricle of said human heart.

19. A stimulator according to claim 9 or claim 10 or claim 15 further comprising means for defining a third heart rate above said second rate, wherein said pulse generator means is responsive to said means for defining said third heart rate, such that said pulse generator means provides said stimulus pulses to said electrode means only when the rate of said human heart is above said third heart rate.

20. A stimulator according to claim 19 wherein said means for defining said second heart rate and said third heart rate comprise means for defining said second and third heart rates as a function of said physiologic parameter.

21. A stimulator according to claim 9 or claim 10 or claim 15, further comprising means for defining a second rate below said first rate and further comprising deactivating means responsive to said sensing means for terminating the operation of said pulse generator means in response to the rate of said heart persistently falling below said second rate.

* * * * *